US012593968B2

(12) United States Patent
Newton et al.

(10) Patent No.: US 12,593,968 B2
(45) Date of Patent: Apr. 7, 2026

(54) SYSTEMS AND METHODS FOR DATA COMMUNICATION VIA A LIGHT CABLE

(71) Applicant: Stryker Corporation, Kalamazoo, MI (US)

(72) Inventors: Thomas Newton, Vancouver (CA); Pedro A. Perez, Hollister, CA (US); Paul Oh Hwang, San Jose, CA (US); Benjamin Hyman Feingold, San Francisco, CA (US); Vitaliy I. Tkachenko, Vancouver (CA)

(73) Assignee: Stryker Corporation, Portage, MI (US)

( * ) Notice: Subject to any disclaimer, the term of this patent is extended or adjusted under 35 U.S.C. 154(b) by 507 days.

(21) Appl. No.: 18/063,062

(22) Filed: Dec. 7, 2022

(65) Prior Publication Data

US 2023/0172445 A1 Jun. 8, 2023

Related U.S. Application Data

(60) Provisional application No. 63/265,150, filed on Dec. 8, 2021.

(51) Int. Cl.
| | |
|---|---|
| *A61B 1/07* | (2006.01) |
| *A61B 1/00* | (2006.01) |
| *A61B 1/06* | (2006.01) |

(52) U.S. Cl.
CPC ............ *A61B 1/07* (2013.01); *A61B 1/00016* (2013.01); *A61B 1/00059* (2013.01); *A61B 1/0655* (2022.02); *A61B 1/0669* (2013.01)

(58) Field of Classification Search
None
See application file for complete search history.

(56) References Cited

U.S. PATENT DOCUMENTS

| | | | |
|---|---|---|---|
| 6,689,050 B1 * | 2/2004 | Beutter | A61B 1/045 |
| | | | 600/117 |
| 2003/0174205 A1 * | 9/2003 | Amling | A61B 1/042 |
| | | | 600/101 |
| 2008/0218355 A1 | 9/2008 | Downie | |
| 2010/0080554 A1 | 4/2010 | Aguren | |
| 2012/0126949 A1 | 5/2012 | Downie | |

(Continued)

FOREIGN PATENT DOCUMENTS

| | | | | |
|---|---|---|---|---|
| DE | 102015009507 A1 * | 1/2017 | ......... | A61B 1/00009 |
| EP | 3378375 A1 | 9/2018 | | |

OTHER PUBLICATIONS

International Preliminary Report on Patentability mailed Jun. 20, 2024, directed to International Application No. PCT/US2022/081099; 9 pages.

(Continued)

*Primary Examiner* — John P Leubecker
(74) *Attorney, Agent, or Firm* — Morrison & Foerster LLP

(57) ABSTRACT

A light cable for conveying light from a light source to an endoscope includes a first connector at a proximal end of the light cable for connecting to the light source; a second connector at a distal end of the light cable for connecting to the endoscope; a light guide for conveying light received from the light source to the endoscope; a first wireless antenna positioned at the proximal end for wireless communication with the light source; and a second wireless antenna positioned at the distal end for wireless communication with the endoscope.

17 Claims, 9 Drawing Sheets

(56) References Cited

U.S. PATENT DOCUMENTS

| | | | |
|---|---|---|---|
| 2012/0256005 A1 | 10/2012 | Kotyrba | |
| 2012/0274452 A1* | 11/2012 | Chamarti | G02B 6/3895 |
| | | | 340/10.5 |
| 2014/0166059 A1* | 6/2014 | Kosugi | A61B 1/00128 |
| | | | 134/113 |
| 2015/0119639 A1* | 4/2015 | Ebata | A61B 1/00059 |
| | | | 600/103 |
| 2015/0272654 A1* | 10/2015 | Esch | A61B 18/1492 |
| | | | 606/34 |
| 2017/0188802 A1* | 7/2017 | Lawrence | A61B 1/0607 |
| 2019/0336217 A1* | 11/2019 | Schubert | A61N 5/0603 |
| 2020/0187758 A1* | 6/2020 | Duckett, III | A61B 1/00114 |

OTHER PUBLICATIONS

International Search Report and Written Opinion mailed May 4, 2023, directed to International Application No. PCT/US2022/081099; 15 pages.
Invitation to Pay Fees mailed Mar. 9, 2023, directed to International Application No. PCT/US2022/081099; 9 pages.

* cited by examiner

800

CONNECT A LIGHT CABLE TO A LIGHT SOURCE THAT IS CONFIGURED TO GENERATE LIGHT FOR PROVIDING TO AN ENDOSCOPE VIA THE LIGHT CABLE — 802

WIRELESSLY TRANSMIT DATA FROM THE LIGHT CABLE TO AN RFID READER OF THE LIGHT SOURCE — 804

900

WIRELESSLY TRANSMIT DATA FROM AN RFID READER OF THE LIGHT SOURCE TO A LIGHT CABLE — 902

STORE THE DATA ON A MEMORY OF THE LIGHT CABLE OR ENDOSCOPE — 904

SYSTEMS AND METHODS FOR DATA COMMUNICATION VIA A LIGHT CABLE

CROSS-REFERENCE TO RELATED APPLICATIONS

This application claims the benefit of U.S. Provisional Application No. 63/265,150, filed Dec. 8, 2021, the entire contents of which are hereby incorporated by reference herein.

FIELD

This disclosure relates generally to medical imaging, and more specifically, to medical imaging utilizing a light cable.

BACKGROUND

An endoscopic camera system includes an endoscope that can be inserted into the body of a patient for delivering light to and receiving light from a surgical cavity. The endoscope is mounted to a camera head that can capture images and video from the light received from the surgical cavity via the endoscope. The camera head is communicatively coupled to a camera control unit that processes video and image data from the camera head for display or storage.

The light required for endoscopic imaging is directed to the endoscope via a light cable. The light cable is connected at one end to a light cable port on the endoscope and at the other end to a light source. The light source includes one or more light engines that generate the light required for imaging. The light cable includes a light guide, such as fiber optics, that extend the length of the light cable to convey light from the light source to the endoscope. Conventionally, the light cable is connectable to and disconnectable from both the endoscope and the illuminator. The light cable and endoscope are typically reusable and one or both may be sterilized between uses.

Endoscopes and light cables can affect the imaging of the endoscopic camera system. Different endoscopes may provide different amounts of illumination to the surgical cavity and may provide a different field of view. Different types of light cables may have different light carrying capacity or efficiency and may deteriorate over time such that they direct less light to the endoscope over time. However, the endoscopic camera system typically does not have any direct information about the endoscope or light cable that are being used.

SUMMARY

According to various aspects, a light cable for connecting an endoscope to a light source includes a wireless antenna at its proximal end for wireless communication with the light source and a wireless antenna at its distal end for wireless communication with the endoscope. The endoscope includes an RFID tag that the light source can read via signals transmitted wirelessly to and from the light cable. The RFID tag may store information associated with the endoscope that can be read by the RFID reader of the light source. This information can be used by the light source or communicated to other systems communicatively connected to the light source. This communication capability does not require wired connections between the light cable and endoscope, which is advantageous over wired connections that could deteriorate over time through repeated cycles of use and/or sterilization.

According to an aspect, a light cable for conveying light from a light source to an endoscope includes a first connector at a proximal end of the light cable for connecting to the light source; a second connector at a distal end of the light cable for connecting to the endoscope; a light guide for conveying light received from the light source to the endoscope; a first wireless antenna positioned at the proximal end for wireless communication with the light source; and a second wireless antenna positioned at the distal end for wireless communication with the endoscope.

Optionally, the light cable includes a, e.g. passive, repeater connecting the first wireless antenna and the second wireless antenna for conveying signals between the first and second wireless antennas.

Optionally, the, e.g. passive, repeater comprises a pair of wires.

Optionally, the light cable further includes an RFID tag at the proximal end for storing information associated with the light cable. The first wireless antenna can be an antenna for the RFID tag. The RFID tag can be an active RFID tag. Optionally, the light cable includes an RFID reader located at the distal end for reading an RFID tag of the endoscope, wherein the active RFID tag provides power to the RFID reader. The second wireless antenna can be an antenna for the RFID reader.

Optionally, the light cable includes an RFID tag antenna for the RFID tag, wherein the RFID tag antenna is positioned at the proximal end.

According to an aspect, a system for providing light for endoscopic imaging includes at least one light generator for generating light for providing to an endoscope via a light cable; a port for connecting the light cable; and an RFID reader configured to wirelessly receive signals from the light cable when the light cable is connected to the port.

Optionally, the RFID reader comprises an antenna positioned in the port and configured for receiving the signals from at least one antenna positioned in a connector of the light cable. The antenna positioned in the port can be annular and positioned radially outwardly of the at least one antenna positioned in the connector when the connector is connected to the port.

Optionally, the RFID reader is configured to wirelessly transmit data to the light cable. Then the RFID reader can be an RFID transmitter or RFID transceiver, for conciseness herein also referred to as RFID reader. Optionally, the system includes one or more processors, memory, and one or more programs stored in the memory for execution by the one or more processors for updating data stored in memory of the light cable, a component connected to the light cable, or both the light cable and the component connected to the light cable via wireless transmission of data to the light cable.

Optionally, the signals comprise data associated with at least one characteristic of the light cable, the endoscope, or both the light cable and endoscope, and the system further comprises one or more processors, memory, and one or more programs stored in the memory for execution by the one or more processors for controlling the at least one light generator based on the at least one characteristic. Optionally, controlling the at least one light generator based on the at least one characteristic includes controlling a power level of the light provided to the light cable.

Optionally, the signals comprise data associated with at least one characteristic of the light cable, the endoscope, or both the light cable and endoscope, and the system further comprises one or more processors, memory, and one or more programs stored in the memory for execution by the one or more processors for providing a notification to a user associated with a suitability of the light cable, the endoscope, or both the light cable and endoscope for a requested lighting mode.

Optionally, the system comprises the light cable. The light cable can include a passive repeater for conveying signals received at a first wireless antenna located at a first end of the light cable to a second wireless antenna located at a second end of the light cable. The light cable can include an RFID tag that comprises a third wireless antenna, wherein the third wireless antenna is located at the first end for wireless signal transmissions with the RFID reader.

Optionally, the system comprises the endoscope. The endoscope can comprise an RFID tag. The RFID reader and RFID tag can communicate via the passive repeater of the light cable. The light cable can include an RFID tag for storing information associated with the light cable and the RFID tag transmits the signals to the RFID reader. The RFID tag can be an active RFID tag that is wirelessly powered by the RFID reader. The light cable can include an RFID reader for reading an RFID tag of an endoscope connected to the light cable, wherein the active RFID tag provides power to the RFID reader.

Optionally, the signals include data associated with at least one characteristic of the light cable, the endoscope, or both the light cable and endoscope, and the at least one characteristic comprises usage tracking data, service tracking data, type data, or calibration data. It is noted that the method concerns the operating of the light cable and/or the endoscope. There is no functional link between the method and effects produced by the endoscope on the body. The endoscope can be pre-inserted into the body. The method can exclude the step of inserting the endoscope into the body. The method is not a method of treatment of the body.

According to an aspect, a method includes connecting a light cable to a light source that is configured to generate light for providing to an endoscope via the light cable; and wirelessly transmitting data from the light cable to an RFID reader of the light source.

Optionally, the method further includes controlling an aspect of the light generated by the light source based on the data transmitted from the light cable to the RFID reader. The data can include at least one of a light cable type and an endoscope type. Optionally, controlling the aspect of the light comprises selecting a lower power mode based on the at least one of a light cable type and an endoscope type.

Optionally, at least a portion of the data is stored in a memory of the light cable.

Optionally, at least a portion of the data is stored in a memory of the endoscope.

Optionally, at least a portion of the data is stored in a memory of a component connected to the endoscope.

Optionally, prior to the data being transmitted from the light cable to the RFID reader of the light source, the data is received by the light cable via one or more signals wirelessly transmitted to the light cable from the endoscope. The one or more signals can be received at a distal end of the light cable and conveyed along the light cable to a proximal end of the light cable for wireless transmission to the RFID reader of the light source.

Optionally, the method further includes wirelessly transmitting data from the RFID reader to the light cable for storing in a memory of the light cable, a memory of the endoscope, or both.

Optionally, the RFID reader reads data stored in a memory of the light cable and data stored in a memory of an endoscope.

Optionally, the method further includes providing a notification to a user of a suitability of at least one of the light cable and the endoscope for a requested lighting mode.

Optionally, the method further includes enabling or disabling delivery of light from the light source based on the data transmitted from the light cable.

Optionally, the method further includes generating images based on the data transmitted from the light cable to an RFID reader of the light source.

Optionally, the data includes at least on characteristics of at least one of the light cable and the endoscope, and wherein generating images comprises performing image processing based on the at least one characteristic.

It will be appreciated that any of the variations, aspects, features and options described in view of the systems apply equally to the methods and vice versa. It will also be clear that any one or more of the above variations, aspects, features and options can be combined.

BRIEF DESCRIPTION OF THE FIGURES

The invention will now be described, by way of example only, with reference to the accompanying drawings, in which.

DETAILED DESCRIPTION

Figure 1:
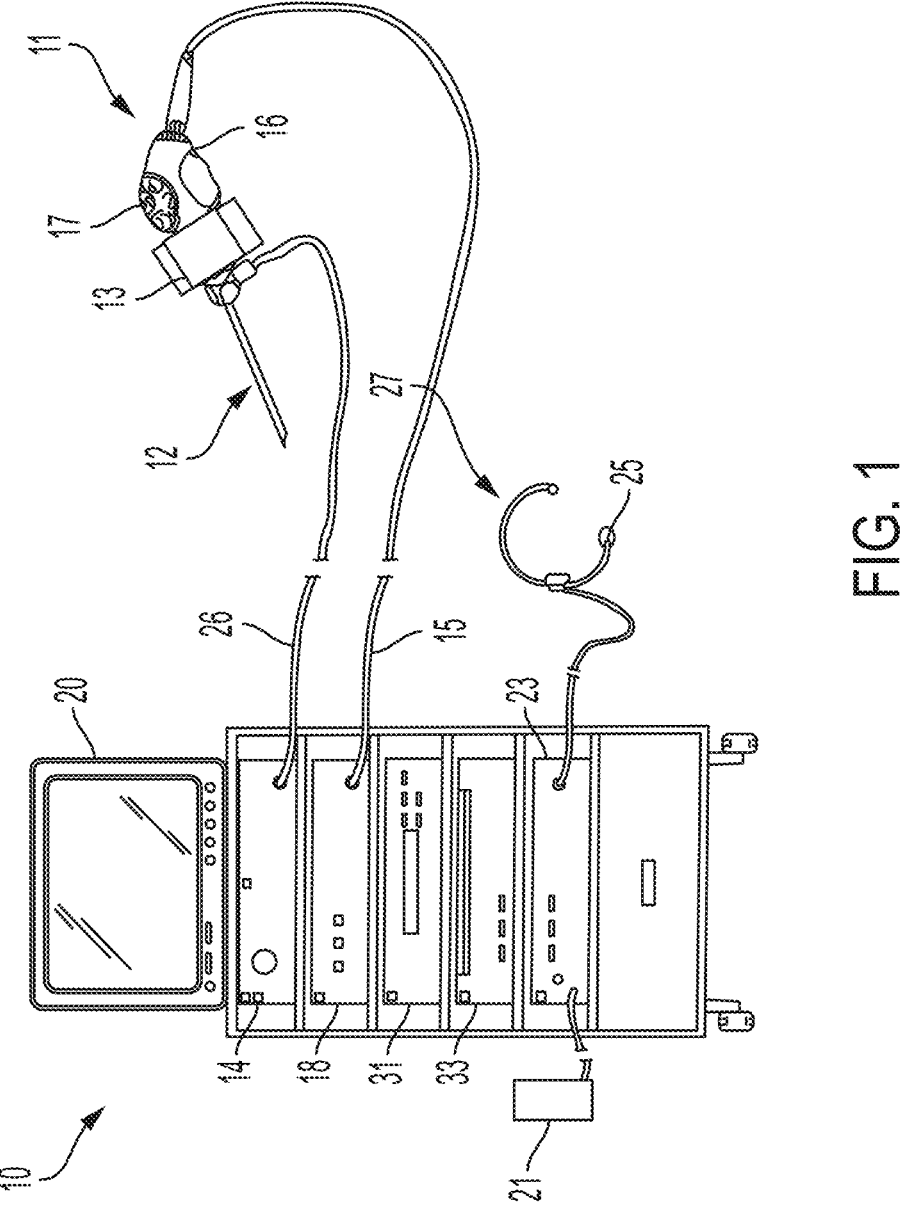
FIG. 1 illustrates an example of an endoscopic imaging system.

Reference will now be made in detail to implementations and examples of various aspects and variations of systems and methods described herein. Although several exemplary variations of the systems and methods are described herein, other variations of the systems and methods may include aspects of the systems and methods described herein combined in any suitable manner having combinations of all or some of the aspects described.

Described herein are devices, systems, and methods for wireless communication between an endoscope and a light source via a light cable. According to various examples, the light cable includes a wireless antenna at its proximal end for wireless communication with the light source and a wireless antenna at its distal end for wireless communication with the endoscope. The endoscope may include an RFID tag that may be read by an RFID reader in the light source via signals wirelessly transmitted to and/or from the light source via the antenna at the proximal end of the light cable, transmitted along the light cable via wiring of the light cable, and wirelessly transmitted to and/or from the endoscope via the antenna at the distal end of the light cable. In some examples, the light cable can include an RFID tag that can be read by the light source. The RFID tags can be passive tags that receive their energy from the signals received from the RFID reader of the light source. Thus, the light cable and/or endoscope does not need to be provided with batteries.

According to various aspects, a processor of the light source is configured to control a controller of the RFID reader of the light source to communicate with one or more RFID tags of a light cable attached to the light source and/or an endoscope attached to the light cable. The RFID reader controller can be configured for driving a carrier signal, a message signal, receiving the incoming signals from the RFID tag(s) (for example, the tag of a connected light cable and/or the tag of a connected endoscope), and managing communication with multiple tags at once, if needed. The RFID reader controller may be connected to a matching network of capacitors, inductors, and/or resistors that tune the signal for the RFID reader antenna. The RFID reader antenna is positioned in the light source such that the RFID reader antenna will be near the light cable antenna(s) to achieve strong enough inductive coupling. When a light cable is plugged into the light source, the antenna(s) located at the proximal end of the light cable couple with the RFID reader antenna. The RFID reader IC sends out polling messages to look for any tags that are coupled to the magnetic field generated by the RFID reader antenna. The light cable may include an RFID tag that couples directly with the RFID reader antenna. An endoscope RFID tag may couple via a, e.g. passive, repeater located in the light cable or an RFID reader of the light cable may read from the endoscope RFID tag and may transmit the information to an RFID tag located at the proximal end of the light cable that is coupled to the RFID reader of the light source. Once the RFID reader controller finds coupled tags, it can read and/or write to the memory of each individual tag. The RFID reader controller can then communicate the information from the tags back to the one or more processors in the light source, which may use the information directly or may transmit the information on to one or more other systems, such as a medical room controller.

The ability for the light source to communicate with the light cable and/or endoscope provides a number of advantages, including allowing the light source to know whether the endoscope is connected to the light cable and the light cable is connected to the light source. Additionally, information associated with the endoscope and/or light cable can be stored in memory of the endoscope and/or light cable for providing the light source and/or other components of the imaging system information about the endoscope and/or light cable. This can provide the imaging system with a number of advantages over conventional systems, including enabling the imaging system to track the service lifetime of the light cable and endoscope, adjust the imaging (e.g., image acquisition and/or image post-processing) for the endoscope type and/or particular endoscope being used, have the light source read the serial number and manufacturing date of the scope and light cable, enable/disable certain light source modes based on the type of light cable and scope that are attached, detect which type of light cable is connected, and/or detect which type of scope is connected.

In the following description, it is to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating" or the like, refer to the action and processes of a computer system, or similar electronic computing device, that manipulates and transforms data represented as physical (electronic) quantities within the computer system memories or registers or other such information storage, transmission, or display devices.

The present disclosure in some examples also relates to a device for performing the operations herein. This device may be specially constructed for the required purposes, or it may comprise a general purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

FIG. 1 shows an example of an endoscopic imaging system 10, which includes an endoscopic camera system 11 that may be utilized in endoscopic procedures. The endoscopic camera system 11 incorporates an endoscope 12 which is coupled to a camera head 16 by a coupler 13 located at the distal end of the camera head 16. Light is provided to the endoscope 12 by a light source 14, which can be configured according to the principles described herein. The light source 14 can provide light to the endoscope 12 via a light guide 26, such as a fiber optic cable. The camera head 16 is connected to a camera control unit (CCU) 18 by an electrical cable 15. The CCU 18 is connected to, and communicates with, the light source 14. Operation of the camera 16 is controlled, in part, by the CCU 18. The cable 15 conveys video image and/or still image data from the camera head 16 to the CCU 18 and may convey various control signals bi-directionally between the camera head 16 and the CCU 18.

A control or switch arrangement 17 may be provided on the camera head 16 for allowing a user to manually control various functions of the system 10, which may include switch from one imaging mode to another, which in some examples, may cause the light source 14 to switch illumination modes, as discussed further below. Voice commands may be input into a microphone 25 mounted on a headset 27 worn by the practitioner and coupled to the voice-control unit 23. A hand-held control device 21, such as a tablet with a touch screen user interface or a PDA, may be coupled to the voice control unit 23 as a further control interface. In the illustrated example, a recorder 31 and a printer 33 are also coupled to the CCU 18. Additional devices, such as an image capture and archiving device, may be included in the system 10 and coupled to the CCU 18. Video image data acquired by the camera head 16 and processed by the CCU 18 is converted to images, which can be displayed on a monitor 20, recorded by recorder 31, and/or used to generate static images, hard copies of which can be produced by the printer 33.

As described further below, endoscopic imaging system 10 can be configured for wireless communication between the light source 14 and the endoscope 12 and/or light cable 26, which can enable the imaging system 10 to know that the endoscope 12 and/or light cable 26 are connected and to know information about the endoscope 12 and/or light cable 26 that are connected. Any suitable wireless communication protocols can be used, including, for example, ISO/IEC 18092, Information technology—Telecommunications and information exchange between systems—Near Field Communication—Interface and Protocol (NFCIP-1), ISO/IEC 15693, Cards and security devices for personal identification—Contactless vicinity objects, ISO/IEC 14443, Cards and security devices for personal identification—Contactless proximity objects, and ISO/IEC 18000, Information technology—Radio frequency identification for item management.

Figure 2:
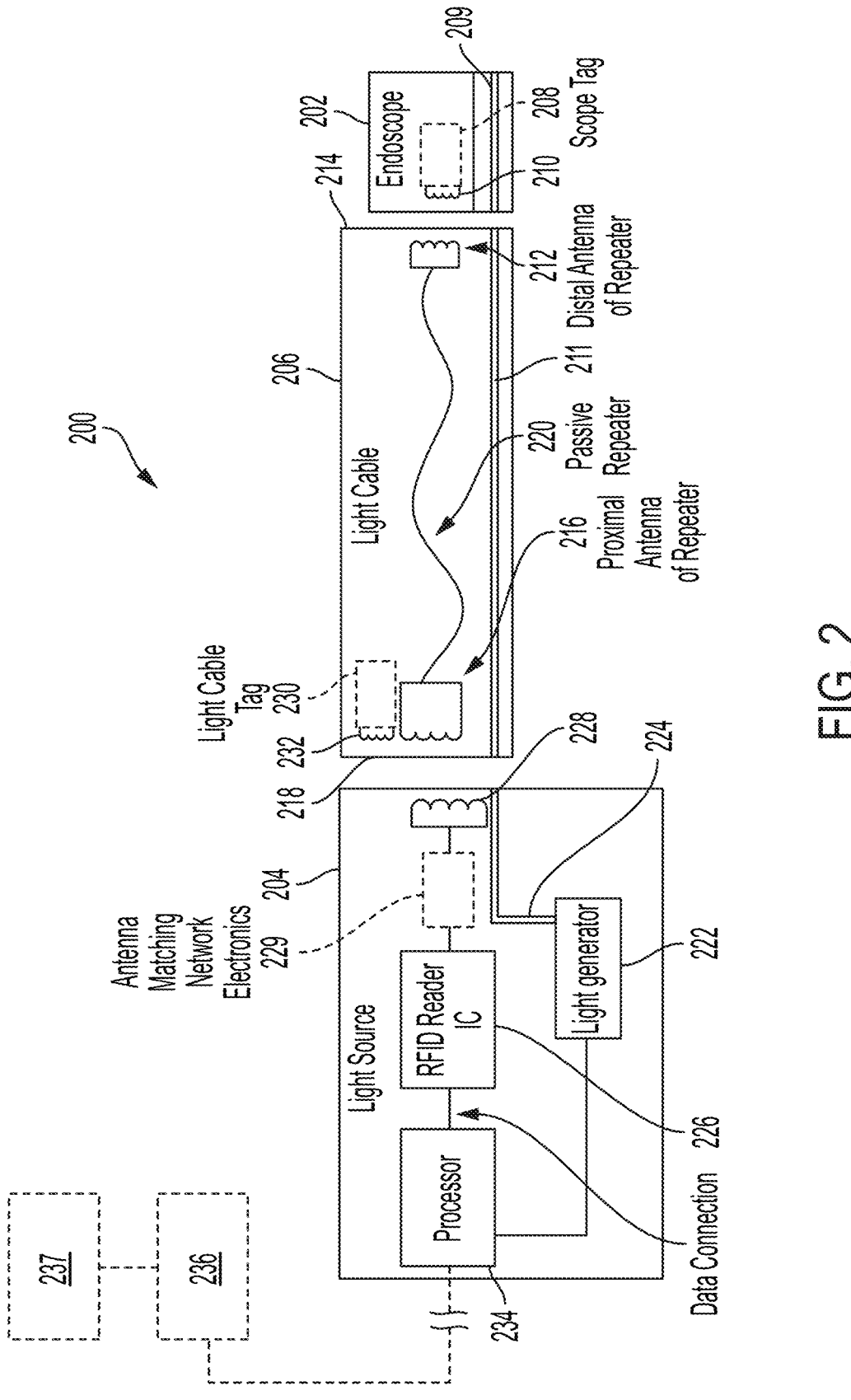
FIG. 2 is a functional block diagram of an illumination apparatus that enables wireless communication with an endoscope.

FIG. 2 is a functional block diagram of an illumination apparatus 200 that enables wireless communication with an endoscope. Apparatus 200 can be a portion of an illumination system, such as illumination system 10 of FIG. 1. Apparatus 200 includes an endoscope 202 for connecting to an endoscopic camera head, such as camera head 16 of FIG. 1, a light source 204 for generating light for endoscopic imaging, and a light cable 206 for conveying the light from the light source 204 to the endoscope 202.

The endoscope 202 can include an RFID tag 208, which as is well known in the art, includes a radio transponder that transmits data when triggered by an electromagnetic interrogation pulse from an RFID reader. The RFID tag 208 includes a processor for processing and generating signals. The RFID tag 208 includes non-volatile memory for storing data. The RFID tag 208 includes or is connected to an antenna 210, such as a coil antenna or a patch antenna. The antenna 210 can be incorporated into a port of the endoscope to which the light cable 206 is attached. The RFID tag 208 can be a passive device that does not have its own power source (i.e., it does not have its own battery) and is powered by the electromagnetic interrogation pulse from an RFID reader. In some examples, the RFID tag 208 is an active device that is powered by an on-board power supply. As is well known in the art, the endoscope 202 also includes a light guide 209 for conveying light received from the light cable 206 to the distal tip (not shown) of the endoscope 202.

The light cable 206 includes a light guide 211 for conveying light received from the light source 204 at the proximal end 218 of the light cable 206 to the distal end 214 of the light cable 206. An antenna 212 is located at the distal end 214 of the light cable 206 for transmitting wireless signals to and/or receiving wireless signals from the endoscope 202 when the light cable 206 is attached to the endoscope 202. The antenna 212 could be incorporate into the connector that connects the distal end 214 of the light cable 206 to the port of the endoscope. The light cable 206 includes an antenna 216 at its proximal end 218 for transmitting wireless signals to and/or receiving wireless signals from the light source 204. The antenna 216 could be incorporate into the connector that connects the proximal end 218 of the light cable 206 to the port of the light source 204. Extending between the two antennas 212, 216 is a, e.g. passive, repeater 220. The passive repeater 220 can convey radio frequency signals received by the two antennas 212, 216 between the two antennas 212, 216 without any modification of the signal by powered electronics. The passive repeater 220 can be formed in a number of different ways, including, for example, as a pair of wires, a twisted pair of wires, and a coaxial cable. The passive repeater 220 may include shielding for reducing electromagnetic interference from external sources. In some examples, one or more antenna matching networks that comprise one or more passive electrical components for impedance matching may be provided in series or parallel with the antennas and passive repeater.

The light source 204 includes one or more light generators 222 (one is shown for simplicity) for generating light having a desired spectrum and one or more light directing elements 224 for directing the generated light to the light cable 206 connected to the light source 204. The light source 204 includes an RFID reader 226 connected to an antenna 228 that transmits wireless signals to and/or receives wireless signals from the light cable 206 when the light cable 206 is connected to the light source 204. An antenna matching network 229 may be included for impedance matching.

In this example, the RFID reader 226 generates signals that are transmitted wirelessly from the antenna 228 to the antenna 216 located at the proximal end 218 of the light source 204. The radio frequency signals are carried by the passive repeater 220 to the antenna 212 located and the distal end 214 of the light cable 206. The signals are wirelessly transmitted from the antenna 212 to the antenna 210 of the endoscope 202. The RFID tag 208 of the endoscope 202 generates signals that travel the same pathway in reverse. In this way, the light source 204 can communicate wirelessly with the endoscope 202.

In some examples, the light cable 206 includes an RFID tag 230 that can include its own antenna 232. The RFID reader 226 can read the RFID tag 230 via wireless signal transmission between the antenna 228 of the light source 204 and the antenna 232 connected to the RFID tag 230.

Here, the light source 204 includes at least one processor 234 for controlling the RFID reader 226 to communicate with the RFID tag 208 of the endoscope 202 and/or the RFID tag 230 of the light cable 206. In some examples, the processor 234 may control the RFID reader 226 to generate a polling signal that is then emitted by the antenna 228 of the light source 204. The polling signal is received by the antenna 216 located at the proximal end 218 of the light source 204 and travels down the passive repeater 220 to the antenna 212 located at the distal end 214 of the light cable 206. The polling signal emitted from the antenna 212 located at the distal end 214 of the light cable 206 is received by the antenna 210 of the endoscope 202. The RFID tag 208 of the endoscope 202 then generates a signal in response. This signal may include information (such as an identification number) that the processor 234 of the light source 204 may parse to determine that the endoscope 202 is connected and/or other information related to the attached endoscope, such as the type of endoscope, the number of uses of the endoscope, the age of the endoscope, a serial number of the endoscope, calibration information associated with the endoscope, etc. In some examples, the processor 234 communicates with the RFID tag 230 of the light cable 206 in similar fashion.

The at least one processor 234 may receive data from the RFID tag 208 of the endoscope 202 and/or the RFID tag 230 of the light cable 206 that is extracted by the RFID reader 226. In some examples, the processor 234 controls the RFID reader 226 to transfer data to the RFID tag 208 of the endoscope 202 and/or the RFID tag 230 of the light cable 206 for writing to a memory of the endoscope 202 and/or light cable 206. For example, information related to the use of the endoscope and/or light cable during the imaging session may be recorded to a memory of the endoscope and/or light cable.

The processor 234 may control the light generator(s) 222 to generate light for imaging. The processor 234 may control the light generation based on information read from a light cable and/or endoscope by the RFID reader 226. For example, in some examples, the processor 234 may not enable light generation unless the light cable 206 and/or the endoscope 202 are determined to be properly connected based on receiving the required RFID signals from the light cable 206 and/or endoscope 202. This can serve as a safety interlock to ensure that light is not emitted from the light source 204 when no light guide and/or no endoscope is connected. In some examples, the processor 234 may control one or more aspects of the light generated by the light source 204 based on information received from the light cable 206 and/or endoscope 202. For example, a high power light generation mode may only be available when a certain type of endoscope and/or certain type of light cable that is designed for the high power light is attached as determined by the RFID signals received from the endoscope.

In some examples, the processor 234 may communicate information related to attachment of the light cable 206 and/or endoscope 202 to one or more external imaging system components 236, such as a camera controller or imaging system controller. For example, an imaging system controller may receive information from the light source 204 indicating whether the endoscope 202 and/or light cable 206 are connected to the light source 204 and the imaging system controller may provide a notification to the user accordingly, such as on a display 237 of the imaging system. The notification can include whether or not a light cable and/or endoscope are attached and/or what type of endoscope and/or light cable are attached. In some examples, information related to the light cable and/or endoscope may be used to control imaging, such as to control the gain of an imaging sensor based on the expected amount of light provided by a particular type of endoscope and/or light cable.

The antennas 210, 212, 216, 228, and 232 can be any suitable configuration, including coil antennas, patch antennas, square spiral antenna, etc. The light cable 206 and/or endoscope 202 may be configured to be autoclavable. The light cable 206 and/or endoscope 202 may be configured to endure hundreds of autoclave cycles without a degradation in performance. The RFID tags and associated antennas may be specially configured to withstand the environment required for cleaning, such as autoclaving, chemical sterilization, etc.

According to an aspect of the disclosure, the light cable 206 can be preassembled to the endoscope 202, rather than being connectable/disconnectable from the endoscope. During use, the preassembled endoscope/light cable may be unpackaged (e.g., removed from a sterile bag or other wrapping), the proximal end of the light cable may be connected to the light source 204, and the endoscope and light cable may be used in the normal fashion. After use, the preassembled light endoscope/light cable may be cleaned (e.g., sterilized) as a preassembly for a subsequent use. Such preassembly may be useful to ensure that the correct type of light cable is used with the endoscope. The proximal end of the light cable can be configured for communicating wirelessly with the light source, as discussed above. Since the preassembled light cable and endoscope do not need to be disconnected from one another by the user, there may be no wireless communication between the distal end of the light cable and the endoscope. In some examples, a wired connection between the endoscope and the light cable enables data to be communicated from a memory of the endoscope to the light source via the wireless communication between the proximal end of the light cable and the light source. In some example, a single memory stores data for both the light cable and the endoscope. The memory may be located in the light cable or in the endoscope.

Figure 3B:
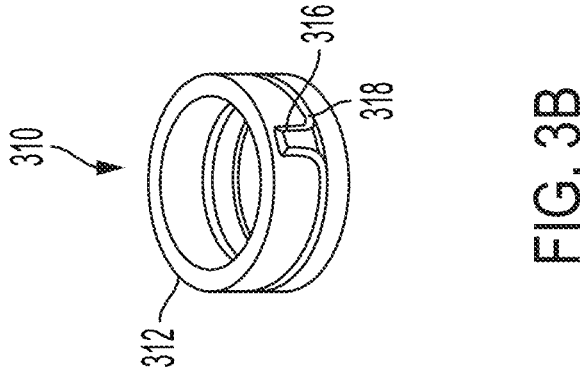
FIG. 3B illustrates an example of an RFID tag assembly for an endoscope.
Figure 3A:
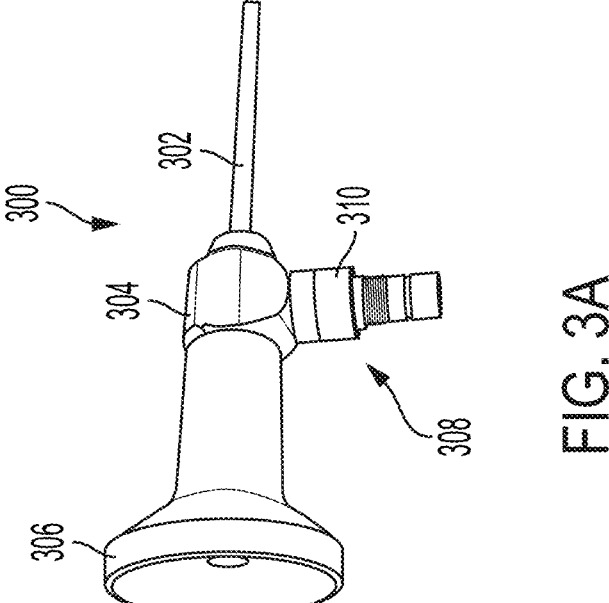
FIG. 3A illustrates the proximal end of an exemplary endoscope that includes wireless communication capability.

FIGS. 3A and 3B illustrate an example of the integration of an RFID tag and antenna into an endoscope, such as for endoscope 202 of FIG. 2. FIG. 3A illustrates the proximal end of an endoscope 300. The endoscope 300 includes an elongated and generally hollow tube 302 that, as is well known in the art, can be inserted into a body cavity, such as through the lumen of a trocar. The tube 302 can be inserted into a natural or pre-made body cavity. The tube 302 can be pre-inserted. The tube 302 extends from a main body 304 to which an eyepiece 306 is attached to provide a viewing port through which a surgeon views the surgical field (for example, directly or through a connection between a viewing port, an endoscopic camera, and a display screen). A light cable port 308 extends from the main body 304 for connecting the endoscope 300 to a light cable to transmit light to a target via the endoscope 300. As is well known in the art, a light guide extends from the port 308, through the main body 304, and along the tube 302 to the distal end where the light carried by the light guide is emitted.

In the illustrated example, an RFID tag assembly 310 is integrated with the light cable port 308. The RFID tag assembly 310 is shown in more detail in FIG. 3B. The RFID tag assembly 310 includes an annular body 312 for mounting onto a collar 314 of the light cable port 308. Integrated into or mounted on the body 312 is an RFID tag 316 and an antenna 318. The antenna 318 may be formed of a coil of wiring that extend circumferentially around the axis of the body 312. The body 312 may be attached to the light cable port 308 in any suitable way, including via an adhesive or a press fit. The body 312 may be formed of a non-metallic material, such as a plastic material, to reduce interference with radio frequency signals transmitted by or to the antenna 318.

Figure 4:
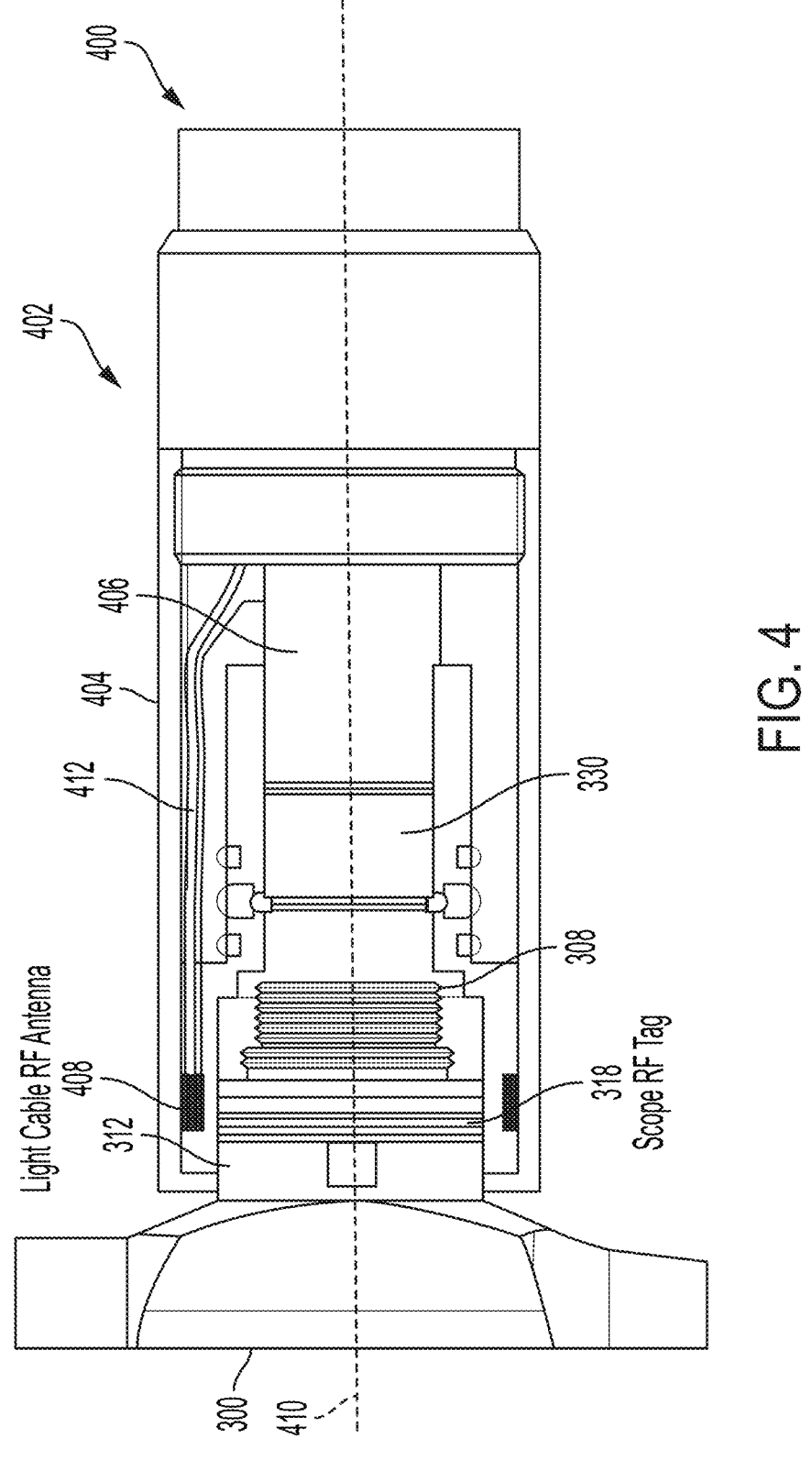
FIG. 4 illustrates an example of the connection of a light cable to the light cable port of an endoscope.

FIG. 4 illustrates an example of the connection of a light cable 400 to the light cable port 308 of endoscope 300 of FIG. 3A. The distal end 402 of the light cable 400 includes a connector 404 that is positioned over the light cable port 308 when the light cable 400 is connected to the endoscope 300. The light cable 400 includes a light guide 406 that aligns with a light guide 330 of the light cable port 308. An antenna 408 is located at the distal end of the light cable 400 for transmitting signals to and/or receiving signals from the antenna 318 mounted to the annular body 312 of the endoscope 300. The antenna 408 can be a number of loops of wire that extend circumferentially about the longitudinal axis 410 of the connector 404. The antenna 408 may be spaced radially outwardly from the antenna 318 incorporated in the body 312 of the light cable port 308. The antennas 408, 318 may partially or entirely overlap in the longitudinal direction of the cable or may not overlap at all. The illustrated locations of the antennas 408, 318 is merely exemplary and other arrangements are within the scope of the disclosure. For example, in some examples, the antennas 408, 318 are located at the same radial position and are spaced in the longitudinal direction from one another. Here, a passive repeater 412 extends proximally from the antenna 408 and extends along the light guide 406 toward the proximal end of the light cable 400.

Figure 5:
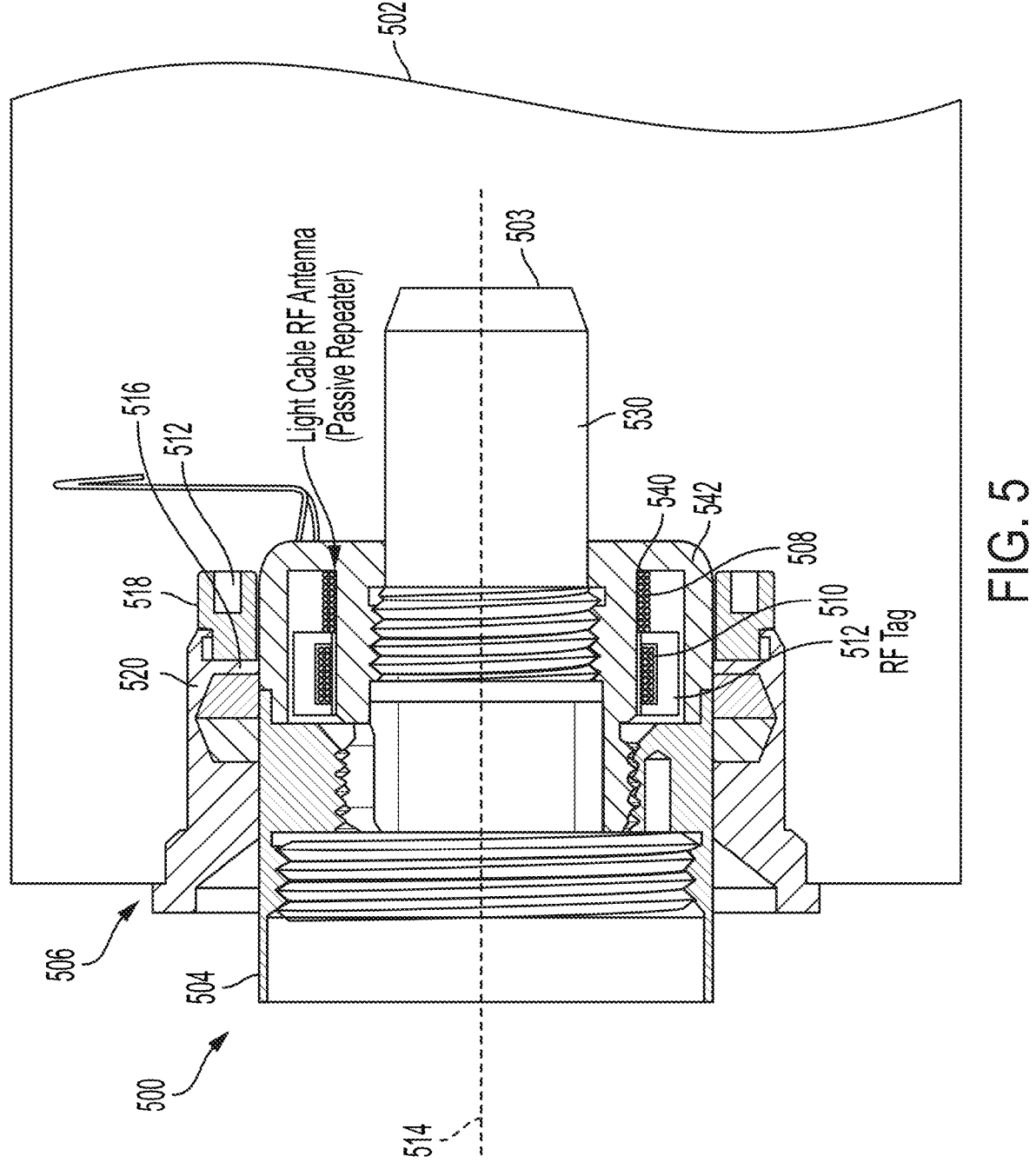
FIG. 5 illustrates an example of a proximal end of a light cable connected to a light source.

FIG. 5 illustrates an example of a proximal end of a light cable 500 connected to a light source 502. The light cable 500 includes a proximal end connector 504 that fits into a light cable port 506 of the light source 502. The connector 504 includes a light guide portion 503 for receiving light from the light source 502. The connector 504 includes an antenna 508 for transmitting signals to and/or receiving signals from the light source 502. The antenna 508 can be a coil of wire that extends radially outwardly of the light guide portion 503 relative to the longitudinal axis 514 of the connector 504. Here, the antenna 508 is connected to a passive repeater that extends from the distal end of the light cable 500 (see, for example, passive repeater 412 of FIG. 4).

In the illustrated example, the connector 504 includes a second antenna 510 that is connected to an RFID tag for the light cable 500. The antenna 510 and connected RFID tag can be mounted in an annular body 512 in similar fashion to the RFID tag assembly 310 shown in FIG. 3B. In the illustrated example, the antenna 510 is adjacent to the antenna 508. The antenna 510 can be at the same radial position as the antenna 508 or radially inward or radially outward of the antenna 508.

The port 506 of the light source 502 includes an antenna 512 that is connected to an RFID reader (see, for example, RFID reader 226 of FIG. 2). The antenna 512 is configured to transmit signals to and receive signals from antenna 508 and antenna 510. In the illustrated example, the antenna 512 is positioned radially outwardly of the antenna 508 and overlaps with the antenna 510 in the longitudinal direction.

The arrangement of antennas 508, 510, and 512 illustrated in FIG. 5 is merely exemplary. More generally, the antennas 508, 510, and 512 are positioned to provide sufficient signal strength when the connector 504 is positioned in the port 506. In some examples, the antennas are arranged such that the signal strength is sufficiently low that the RFID reader of the light source 502 cannot detect the light cable 500 when the connector 504 is adjacent to the port 506 of the light source 502 but not inserted within the port 506. In some examples, the antennas are arranged such that the signal strength is sufficiently low that the RFID reader of the light source cannot detect the light cable 500 when the connector 504 is partially but not fully inserted in the port 506, which may be advantageous when the RFID-based signal detection is used as a safety interlock for preventing light generation when the light cable 500 is not fully inserted in the port 506.

In some examples, the light source, light cable, and/or endoscope can include features for steering radio frequency energy toward the antenna(s) of the light cable and/or endoscope. For example, ferrite material may be positioned between one or more antenna(s) and metal materials in the vicinity of the one or more antenna(s). For example, ferrite material may be positioned at an interface 516 between a mounting body 518 of the antenna 512 and a contact ring 520 of the port 506 so that the magnetic field generated by the antenna 512 is not dissipated by the metal contact ring 520. Additionally or alternatively, ferrite material may be positioned between the antenna 508 and/or antenna 510 and a metal ferrule 530 of the light guide portion 503, such as positioned along a surface 540 of a mounting body 542 for the antennas 508, 510.

Figure 6:
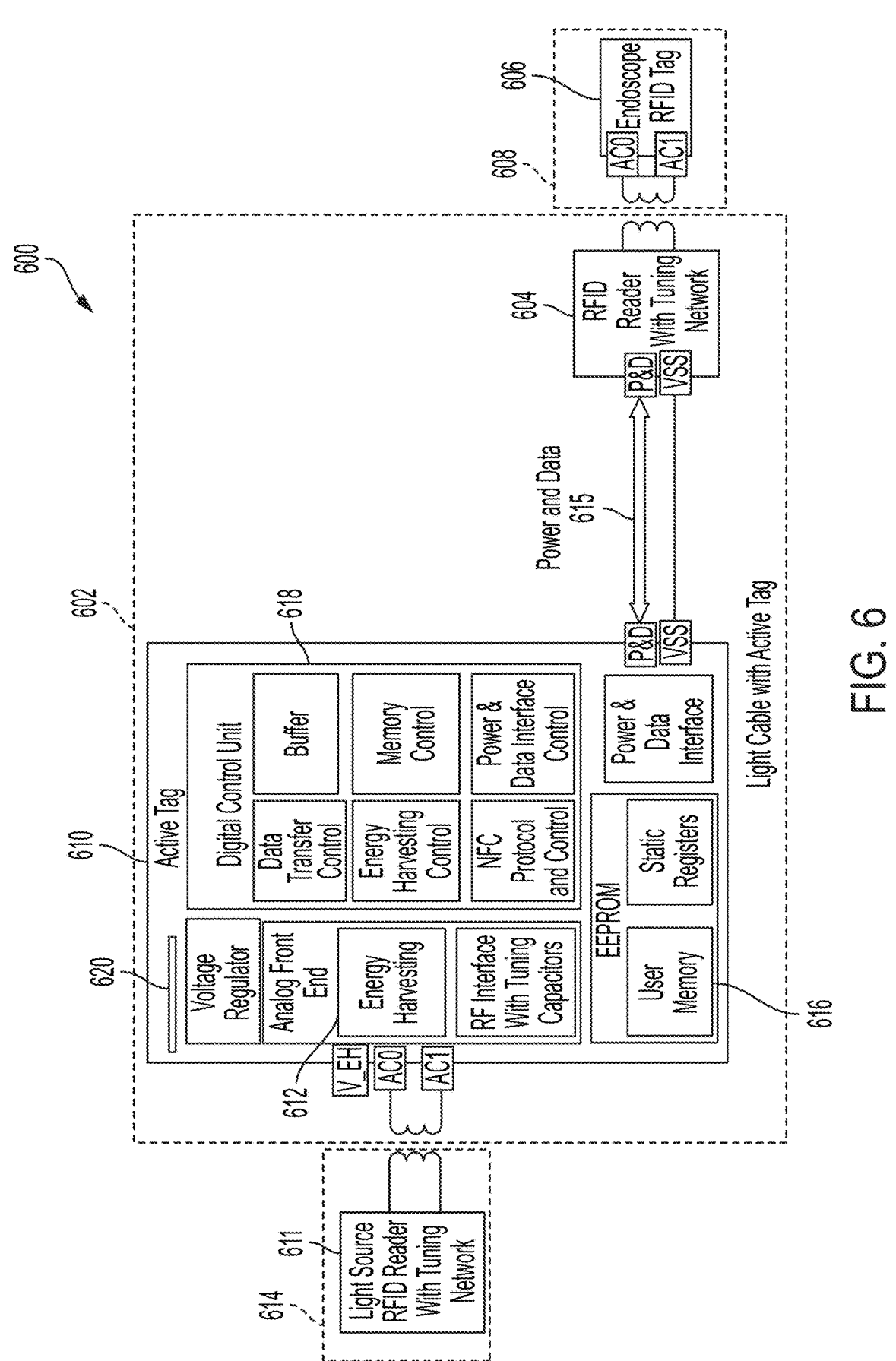
FIG. 6 is a block diagram of a system for wireless communication between a light source, light cable, and endoscope in which the light cable includes an RFID reader at its distal end for communicating with the RFID tag of the endoscope.

FIG. 6 is a block diagram of a system 600 for wireless communication between a light source, light cable, and endoscope in which the light cable includes an RFID reader at its distal end for communicating with the RFID tag of the endoscope. The RFID reader of the light cable is powered by an active RFID tag at the proximal end of the light cable. As used herein, active RFID tags encompass tags conforming to Bluetooth and Bluetooth Low Energy standards. The active RFID tag can charge its on-board power supply 620 via signals received wirelessly from the RFID reader of the light source.

System 600 includes a light cable 602 that includes an RFID reader 604 at its distal end for wirelessly communicating with an RFID tag 606 of an attached endoscope 608. The RFID reader 604 is powered by and communicates with an active RFID tag 610 that can be located at the proximal end of the light cable 602. The active RFID tag 610 and RFID reader 604 can communicate with each other via a digital communication over a wired connection 615. This is in contrast to light cable 206 of FIG. 2 in which the passive repeater 220 conveys radio frequency signals between the proximal and distal antennas of the light cable.

The active RFID tag 610 is powered by wireless signals received from the RFID reader 611 of the light source 614. The active RFID tag 610 can include an energy harvesting module 612 for harvesting energy from the wireless signals received from the RFID reader 611 for charging the on-board power supply 620. At least a portion of the energy harvested by the energy harvesting module 612 is used to power the RFID reader 604 at the distal end of the light cable 602 so that the RFID reader 604 can communicate with the RFID tag 610 of the endoscope 608. Power may be transferred from the active RFID tag 610 to the RFID reader 604 via the wired connection 615. The power may be transferred via the same wiring as the digital communication or via different wiring.

The active RFID tag 610 includes a memory 616 for storing data associated with the light cable and a controller 618 that can read and write data to the memory 616, control the power harvesting module 612, parse the data received from the RFID reader 611, and control the transmission of power and data to the RFID reader 604.

Figure 7A:
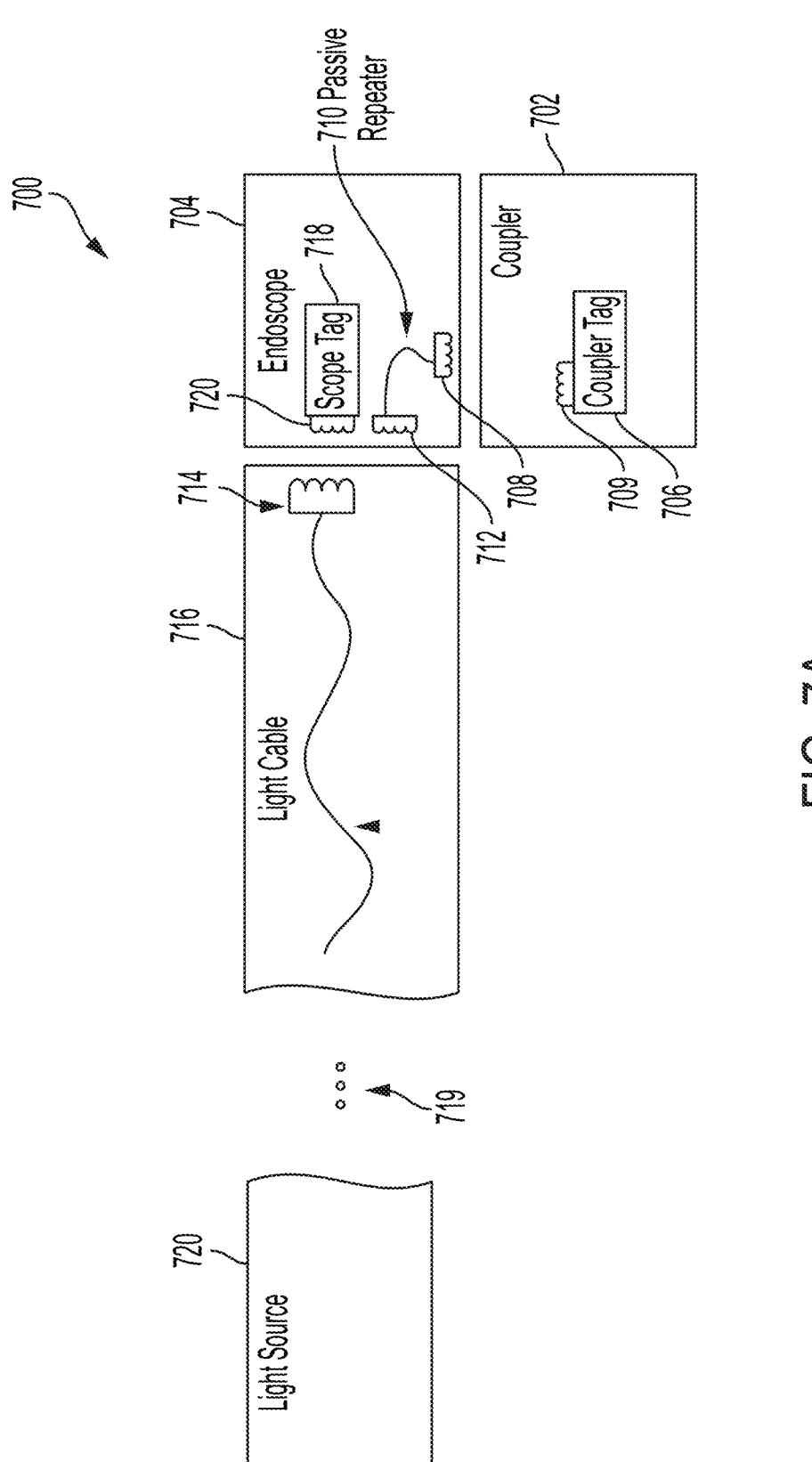
FIG. 7A is a block diagram of a system that includes a coupler used for coupling the endoscope to a camera head.

As discussed above, a light source can communicate with an endoscope via the light cable. In some examples, the light source can communicate with a component connected to the endoscope such as a coupler (see, for example, coupler 13 of FIG. 1) that couples the endoscope to an endoscopic imaging head. FIG. 7A is a block diagram of a system 700 that includes a coupler 702 used for coupling the endoscope 704 to a camera head (not shown). The coupler 702 includes an RFID tag 706 that has memory for storing information associated with the coupler 702. The information can include, for example, an identifier that enables the system 700 to identify that the coupler 702 is being used. The information could additionally or alternatively include the number of uses of the coupler 702, the lifespan of the coupler 702, a type of the coupler 702, service history of the coupler 702, or any other useful information.

The endoscope 704 includes an antenna 708 for communicating with the antenna 709 of the RFID tag 706. The antenna 708 can be located in a portion of the endoscope 704 that is proximate to the coupler 702 when the endoscope 704 and coupler 702 are coupled. For example, the antenna 708 can be incorporated in the eyepiece of the endoscope 704.

The antenna 708 can be connected via a, e.g. passive, repeater 710 to an antenna 712 that is located in the light port of the endoscope 704 for wirelessly transmitting signals to and receiving signals from the antenna 714 at the distal end of the light cable 716. As discussed above, radio frequency signals are carried by the passive repeater 710 between the two antennas 708, 712.

The endoscope 704 can include its own RFID tag 718 and associated antenna 720 for storing and communicating information for the endoscope 704. The light cable 716 can be configured in similar fashion to light cable 206 of FIG. 2 or light cable 602 of FIG. 6. Alternatively, the light cable 716 can include a wired connection 719 to the light source 720.

Figure 7B:
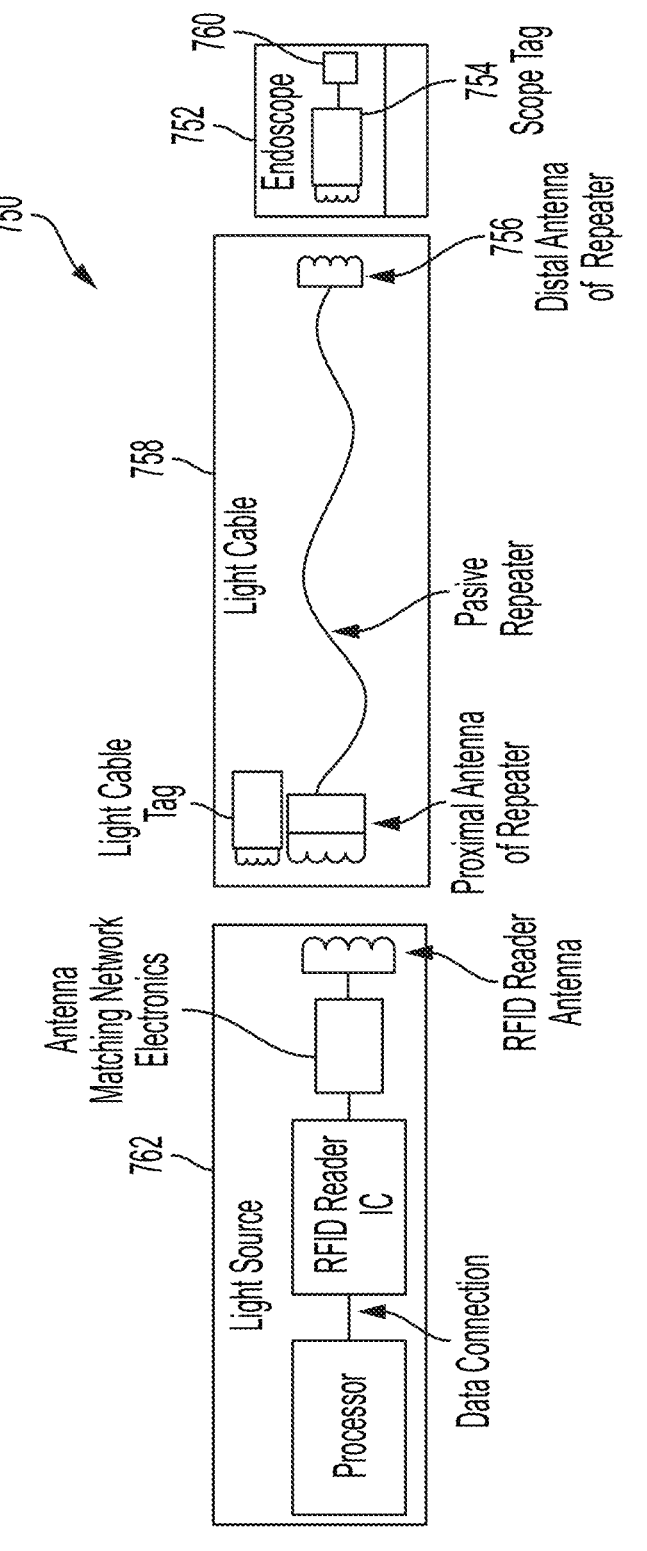
FIG. 7B is a block diagram of a system that uses wireless energy harvesting to power one or more sensors in an endoscope.

As discussed above with regards to system 600 of FIG. 6, energy harvesting can be utilized to power an RFID reader. Energy harvesting can be utilized to power electronics other than RFID readers. For example, energy harvesting can be used to power one or more sensors of an endoscope. An example of this is illustrated in the block diagram of FIG. 7B. System 750 includes an endoscope 752 that includes an energy harvesting system 754 for harvesting energy from wireless signals received from a distal antenna 756 of the light cable 758. The energy harvesting system 754 can be, for example, an active RFID tag that has energy harvesting functionality, such as active RFID tag 610 of FIG. 6. The energy harvesting system 754 can harvest energy from the wireless signals received from the light guide. The harvested energy can be used to power one or more sensors 760 of the endoscope, either directly or via an on-board battery. Examples of sensors that may be powered via harvested energy include temperature sensors, which can be used to monitor the temperature of the endoscope such as to prevent over-temperature or to facilitate endoscope warming for defogging, and gyroscopic sensors, which can be used to determine the orientation of the endoscope such as for feedback for robotic positioning of the endoscope or for determining the orientation of an angled lens at the distal tip of the endoscope. Data from the sensor(s) 760 can be stored in a memory of the endoscope and/or communicated to the light source 762 according to the principles described above. Data from the sensors can be transmitted from the endoscope 752 to the light source 762 periodically based on a predetermined schedule or in response to polling by the light source 762. Signals for use by the energy harvesting system 754 for harvesting energy can be provided by the light source 862 continuously, periodically based on a predetermined schedule, or in response to a request by the energy harvesting system 754.

Figure 8:
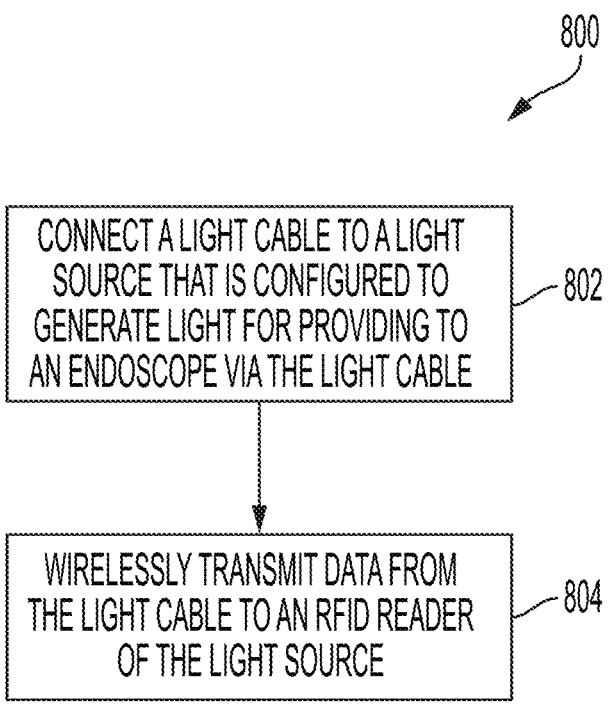
FIG. 8 is a diagram of a method for transmitting data from a light cable to a light source.

FIG. 8 is a diagram of a method 800 for transmitting data from a light cable to a light source. At step 802, a light cable is connected to a light source. The light cable can be, for example, light cable 206 of FIG. 2, light cable 400 of FIG. 4, light cable 500 of FIG. 5, or light cable 716 of FIG. 7A. The light cable includes a connector at its proximal end that is connected to a port of the light source.

The light source may include an RFID reader that broadcasts interrogation signals for communicating with RFID tags, such as an RFID tag of the light cable, an RFID tag of an endoscope connected to the light cable, and/or an RFID tag connected to a component connected to the endoscope (directly or through one or more intermediate components). The RFID reader may be controlled by a processor of the light source, which may direct the RFID reader to check for nearby tags, such as upon startup of the light source, periodically, and/or periodically until a light cable and/or endoscope are attached. In some examples, the RFID reader continuously checks for nearby tags so that the light source can detect when the light cable and/or endoscope are no longer connected.

The antenna of the RFID reader may be located in or near the port of the light source and the power of the RFID reader's signal may be such that the RFID reader is only able to communicate to the light cable or via the light cable when the connector of the light cable is connected to the port. For example, the RFID reader may not be able to communicate with the light cable or via the light cable when the light cable is merely adjacent to the light source but not connected to the light source (e.g., coiled on top of the light source or on the same cart as the light source).

At step 804, data is transmitted wirelessly from the light cable to an RFID reader of the light source. The interrogation signal(s) broadcast from the RFID reader may be received by one or more RFID tags of the light cable, the endoscope, and/or a component connected to the endoscope. The one or more RFID tags may respond by generating radio frequency signals that include data associated with the light cable, endoscope, and/or component connected to the endoscope. The data may originate from a memory of the light cable, on the memory of an endoscope connected to the light source, and/or on a component connected to the endoscope. The radio frequency signals containing the data may be transmitted from an antenna located in the proximal end connector of the light cable to the antenna of the RFID reader of the light source.

Multiple wireless links may be used to transmit the data from its source to the RFID reader of the light source. For example, data stored in a memory of an RFID tag of a coupler may be transmitted across a first wireless link from the coupler to the endoscope, across a second wireless link from the endoscope to the light cable, and then across a third wireless link from the light cable to the light source.

Data transmitted across a wireless link between the endoscope and the distal end of the light cable may be transmitted to the proximal end of the light cable via a wired connection. The wired connection can be a passive repeater, such as passive repeater 220 of FIG. 2, which carries radio frequency signals transmitted across the wireless link. Alternatively, the data can be transmitted digitally from an RFID reader located at the distal end of the light cable to an active RFID tag located at the proximal end of the light cable. The RFID reader located at the distal end of the light cable may be powered by the active RFID tag, and the active RFID tag may harvest the power from the signals received from the RFID reader of the light source.

The data transmitted to the RFID reader of the light source may originate from multiple sources. For example, a portion of the data may come from an RFID tag of the light cable and a portion of the data may come from an RFID tag of the endoscope.

The data transmitted to the RFID reader may include any information relevant to the device storing the data (e.g., light cable, endoscope, and/or other component). The information can include identifying information, such as an identification number (e.g., serial number) associated with the device. The identifying information may indicate the type of device, such as whether the device is a light cable or an endoscope. The information may indicate the type of light cable or the type of endoscope. The information can include historical information, such as a number of uses of the device, an age of the device, service history of the device, and/or repair history of the device.

The data received by the light source can be used in a number of different ways. For example, one or more processors of the light source may analyze the data to determine what is connected and may enable delivery of light based on determining that the light cable is connected and/or the endoscope are detected. In some examples, light delivery may only be enabled when both the light source and endoscope are determined to be connected based on the information received by the RFID reader of the light source.

The light source may control the generation of light based on the data received by the RFID reader. For example, the amount of light generated by the light source may be adjusted according to the type of light cable and/or the type of endoscope, such that, for example, more light is generated when larger light cables and/or endoscopes are connected since larger light cables and/or endoscopes may be able to handle more light power. In some examples, the availability of different modes of light delivery by the light source may depend on the type of light source and/or type of endoscope determined based on the information received via the RFID reader of the light source. For example, a high power light delivery mode (e.g., white light, fluorescence excitation light, etc.) may only be enabled upon determining that an appropriately configured light cable and/or appropriately configured endoscope are attached.

The light source may provide an indication to a user regarding the connected device(s). For example, the light source may indicate on a display (e.g., a display screen and/or one or more LEDs) of the light source when the light cable is connected to the light source and/or when the endoscope is connected to the light cable. In some examples, the light source may indicate to the user a type of the light cable and/or a type of the endoscope connected to the light source.

Information received from the light source, endoscope, and/or other components can be provided to one or more external systems connected to the light source. The light source may transmit at least some of the information to an external system, such as a camera controller, an imaging system controller that controls imaging system components, a medical room controller that controls multiple subsystems of the medical room, a hospital information system, etc. The information can be used in a number of different ways. The information can be used to provide an indication to the user that a light cable and/or endoscope are connected (e.g., displayed on a display screen in the operating room, such as display 20 of FIG. 1). The information can include calibration data that may be used to adjust how images are generated. The calibration data could be specific to the type of endoscope and/or types of light cable or could be specific to the particular endoscope and/or light cable (such as generated during testing at the manufacturing facility). The calibration data could be used, for example, to adjust the gain of an imaging sensor and/or the post-processing of image brightness based on the type of endoscope and/or light cable, such as to adjust for differences in brightness attributable at least in part to the particular endoscope and/or light cable. In some examples, endoscopic images may be cropped differently to account for difference in the field of view resulting from different endoscope sizes. An imaging mode may be enabled or disabled based on the type of light cable and/or endoscope connected to the light source. For example, an imaging mode that requires relatively high power light output may only be available for selection by the user when a properly configured light cable and/or endoscope are connected to the light source.

Information can be used to update records associated with the light cable and/or endoscope. For example, a device tracking log and/or usage log maintained in a hospital information system can be updated to record the location of the light cable and/or endoscope (or other component) and/or to record the usage of the light cable and/or endoscope. This information could be used to schedule preventive maintenance or refurbishment or to retire a light cable and/or endoscope before it adversely affects imaging quality.

Figure 9:
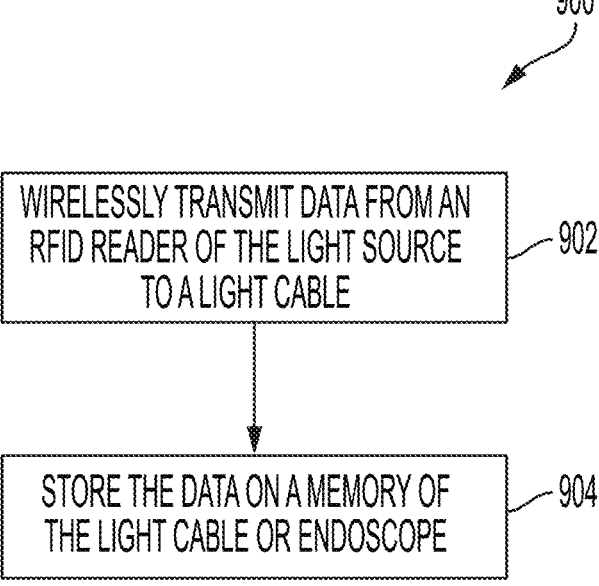
FIG. 9 is a diagram of a method for updating information stored on a light cable or endoscope connected to a light source.

In some examples, information is not only extracted from a light source, endoscope, and/or other component, information can be stored on the light source, endoscope, and/or other component. FIG. 9 is a diagram of a method 900 for updating information stored on a light cable or endoscope connected to a light source. At step 902, data is transmitted wirelessly from an RFID reader of the light source to a light cable. For example, a controller of the light source can control the RFID reader to transmit data wirelessly to the light cable. The data may be directed to an RFID tag of the light cable and/or to an RFID tag of the endoscope and/or component connected to the endoscope (e.g., coupler).

At step 904, data is stored on a memory of the light cable, endoscope, and/or component connected to the endoscope. An RFID tag controller may parse the data received from the RFID reader and save the data to a local memory. In some examples, a first RFID tag parses the data and transmits at least a portion of the data to a second RFID tag for storage on a memory of the second RFID tag. For example, with reference to FIG. 6, controller 618 of active RFID tag 610 may parse the data received from the RFID reader 611 of the light source 614, and based on instructions in that data, may control the RFID reader 604 at the distal end of the light cable 602 to transmit data to RFID tag 606 of the endoscope 608 for storage on a local memory of the RFID tag 606.

The data stored on the memory of the light cable, endoscope, and/or component connected to the endoscope can be, for example, an update to the number of uses of the respective device. For example, at the beginning of an imaging session, the number of uses of the light cable and/or endoscope stored on the respective device can be incremented by one. Similarly, an amount of time (such as a number of minutes or hours) of use of the device can be recorded to its local memory. The light source itself can determine what information to store on the light cable and/or endoscope or the light source may be controlled by an external system (e.g., a medical room controller) to transfer the information to the light cable and/or endoscope.

As described above, information can be read from and/or written to a light cable and/or endoscope attached to a light source without requiring electrical connection between the light source and the light cable and/or without requiring electrical connection between the light cable and the endoscope. This provides the ability for the light source and/or system coupled to the light source to have information about the light cable and/or endoscope attached to the light source without the need for a wired connection that could deteriorate over time from multiple uses and/or multiple sterilizations.

For the purpose of clarity and a concise description, features are described herein as part of the same or separate examples; however, it will be appreciated that the scope of the disclosure includes examples having combinations of all or some of the features described.

The foregoing description, for the purpose of explanation, has been described with reference to specific examples. However, the illustrative discussions above are not intended to be exhaustive or to limit the invention to the precise forms disclosed. Many modifications and variations are possible in view of the above teachings. The examples were chosen and described in order to best explain the principles of the techniques and their practical applications. Others skilled in the art are thereby enabled to best utilize the techniques and various examples with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A system for providing light for endoscopic imaging, the system comprising:
an endoscope comprising an RFID tag;
a light cable comprising an RFID reader configured to communicate with the RFID tag of the endoscope, and an RFID tag communicably coupled to the RFID reader of the light cable; and
a light source, comprising:
at least one light generator for generating light for providing to the endoscope via the light cable;
a port for connecting the light cable; and
an RFID reader configured to wirelessly receive signals from the RFID tag of the endoscope via the RFID tag of the light cable when the light cable is connected to the port.

2. The system of claim 1, wherein the light cable comprises:
a first connector at a proximal end of the light cable for connecting to the light source;
a second connector at a distal end of the light cable for connecting to the endoscope;
a light guide for conveying light received from the light source to the endoscope;
a first wireless antenna positioned at the proximal end for wireless communication with the light source; and
a second wireless antenna positioned at the distal end for wireless communication with the endoscope.

3. The system of claim 1, wherein a wired connection connects the first wireless antenna and the second wireless antenna for conveying signals between the first and second wireless antennas.

4. The system of claim 1, wherein the RFID tag of the light cable stores information associated with the light cable.

5. The system of claim 1, wherein the RFID tag of the light cable is an active RFID tag that is wirelessly powered by the RFID reader of the light source.

6. The system of claim 5, wherein the active RFID tag provides power to the RFID reader of the light cable.

7. The system of claim 1, wherein the RFID reader of the light source comprises an antenna positioned in the port and configured for receiving the signals from at least one antenna positioned in a connector of the light cable.

8. The system of claim 1, wherein the light source further comprises one or more processors, a memory, and one or more programs stored in the memory for execution by the one or more processors for updating data stored in a memory of the light cable, a component connected to the light cable, or both the light cable and the component connected to the light cable via wireless transmission of data to the light cable.

9. The system of claim 1, wherein the signals comprise data associated with at least one characteristic of the light cable, the endoscope, or both the light cable and endoscope, and the system further comprises one or more processors, memory, and one or more programs stored in the memory for execution by the one or more processors for controlling the at least one light generator based on the at least one characteristic.

10. The system of claim 9, wherein controlling the at least one light generator based on the at least one characteristic comprises controlling a power level of the light provided to the light cable.

11. The system of claim 9, wherein the signals comprise data associated with the at least one characteristic of the light cable, the endoscope, or both the light cable and endoscope, and the system further comprises one or more processors, memory, and one or more programs stored in the memory for execution by the one or more processors for providing a notification to a user associated with a suitability of the light cable, the endoscope, or both the light cable and endoscope for a requested lighting mode.

12. The system of claim 1, wherein the signals comprise data associated with at least one characteristic of the light cable, the endoscope, or both the light cable and endoscope, and the at least one characteristic comprises usage tracking data, service tracking data, type data, or calibration data.

13. A method comprising:
connecting a light cable to a light source that is configured to generate light for providing to an endoscope via the light cable; and
wirelessly transmitting data from the light cable to an RFID reader of the light source,
wherein the data is transmitted by the endoscope via one or more signals that are conveyed along the light cable to a proximal end of the light cable for wireless transmission to the RFID reader of the light source.

14. The method of claim 13, further comprising controlling an aspect of the light generated by the light source based on the data transmitted from the light cable to the RFID reader.

15. The method of claim 13, further comprising wirelessly transmitting data from the RFID reader to the light cable for storing in a memory of the light cable, a memory of the endoscope, or both.

16. The method of claim 13, further comprising providing a notification to a user of a suitability of at least one of the light cable and the endoscope for a requested lighting mode.

17. The method of claim 13, further comprising generating images based on the data transmitted from the light cable to the RFID reader of the light source, wherein the data comprises at least one characteristic of at least one of the light cable and the endoscope, and wherein generating images comprises performing image processing based on the at least one characteristic.

* * * * *